United States Patent
Henze et al.

(10) Patent No.: US 6,242,755 B1
(45) Date of Patent: Jun. 5, 2001

(54) METHOD AND DEVICE FOR THE CONTACTLESS MEASURING OF STRAND-LIKE TEXTILE MATERIAL

(75) Inventors: Herbert Henze, Mönchengladbach; Gerhard Rienas, Heinsberg, both of (DE)

(73) Assignee: W. Schlafhorst AG & Co. (DE)

( * ) Notice: Subject to any disclaimer, the term of this patent is extended or adjusted under 35 U.S.C. 154(b) by 0 days.

(21) Appl. No.: 09/350,044

(22) Filed: Jul. 8, 1999

(30) Foreign Application Priority Data

Jul. 8, 1998 (DE) ............................... 198 30 395

(51) Int. Cl.⁷ .................................................. G01N 21/86
(52) U.S. Cl. ............................... 250/559.24; 250/559.12; 250/221
(58) Field of Search ........................... 250/559.24, 559.4, 250/559.26, 559.12, 559.21, 559.29, 221; 356/238.1, 238.2, 384, 385, 379

(56) References Cited

U.S. PATENT DOCUMENTS

| 5,264,909 | 11/1993 | Rochester ........................... 356/73.1 |
| 5,615,014 | * 3/1997 | Okuda ................................. 356/429 |

FOREIGN PATENT DOCUMENTS

| 643 060 A5 | 5/1984 | (CH) . |
| 32 35 492 A1 | 4/1983 | (DE) . |
| 201 500 B1 | 1/1987 | (DE) . |
| 36 12 145 A1 | 10/1987 | (DE) . |
| 37 31 531 A1 | 4/1988 | (DE) . |
| 36 41 816 A1 | 6/1988 | (DE) . |
| 38 34 478 A1 | 4/1990 | (DE) . |
| 41 24 750 A1 | 1/1992 | (DE) . |
| 41 31 664 A1 | 3/1993 | (DE) . |
| 195 23 055 A1 | 1/1997 | (DE) . |
| 38 32 984 C2 | 4/1997 | (DE) . |
| 0 213 587 A2 | 3/1987 | (EP) . |

* cited by examiner

Primary Examiner—Que T. Le
(74) Attorney, Agent, or Firm—Kennedy Covington Lodbell & Hickman, LLP

(57) ABSTRACT

A method for the contactless measuring of strand-like yarn material as well as to a device for carrying out the method. Textile material 4 is irradiated within a measuring range of at least one ray source 1 and imaged on a sensor range of a receiving device 10 comprising sensor cells 8, 11, 12, 14. The signals generated by the individual sensor cells 8, 11, 12, 14 are converted into measured values for the dimensions of material to be measured 4. The signals of the sensor cells 12, 14 covered only partially by the image of the textile material 4 are taken into account in the measured result in a pro rata manner proportional to the amount of the covering.

14 Claims, 3 Drawing Sheets

METHOD AND DEVICE FOR THE CONTACTLESS MEASURING OF STRAND-LIKE TEXTILE MATERIAL

BACKGROUND OF THE INVENTION

The present invention relates to a method and a device for contactless measuring of a strand-like textile material of indeterminate extended length, and more particularly to such a method and device basically operative by irradiating the textile material within a measuring range of at least one ray source, imaging the textile material on a sensor range of a receiving device comprising sensor cells, and converting the signals produced by the individual sensor cells into measured values for the dimensions of the textile material.

In the case of strand-like material such as, e.g., yarns, etc., properties must be continuously measured or monitored in a series of production or processing steps. In particular, properties such as the diameter of the particular material to be measured and its variations require measurements with a high degree of precision.

In order to determine the diameter, Swiss Patent CH 643,060 teaches illuminating a strand-like body by a light source and receiving the illumination state thereby produced by means of an image sensor wherein its photosensors are individually scanned and the local illumination state determined by each photosensor is examined to determine whether it reaches or exceeds a given threshold value. The signals of the photosensors must reach or exceed this threshold value if they are to be considered as a contribution to the total measured value and transformed in an evaluation device into measured values for the diameter of the body. If the signal of a photosensor reaches or exceeds the threshold value the photosensor is evaluated as illuminated. If the signal does not reach the threshold value the photosensor is evaluated as not illuminated. The reference contemplates possible use in yarn cleaners.

A yarn Nm 40 has a diameter of approximately 250 $\mu$m. Suitable and customary image sensors for determining the diameter of such a yarn have a resolution of 10 to 30 $\mu$m. The image resolver described in Swiss Patent CH 643,060 is, e.g., a CCD line sensor which contains 500 photoreceivers or sensor cells in a width of 7.5 mm and thus has a resolution of 15 $\mu$m resulting from the interval and the width of the photoreceiver. Thus, an error of ±6% can occur, conditioned by the method described in it, when determining the diameter, and in other image sensors cited above up to a range of ±10%. However, a measured value with an error of less than 1% is required for yarn cleaning.

SUMMARY OF THE INVENTION

It is accordingly an object of the present invention to provide a method by which the precision of determining the dimensions of the material to be measured is increased and deviations of the determined value from the actual value which occur in the above-described threshold-value method are reduced. It is a further object of the invention to provide a device for carrying out the method.

The invention solves this problem by providing a method and a device for contactless measuring of a strand-like textile material of indeterminate extended length, basically operative for irradiating the textile material within a measuring range of at least one ray source, imaging the textile material on a sensor range of a receiving device comprising sensor cells, and converting the signals produced by the individual sensor cells into measured values for the dimensions of the textile material. According to the present invention, the signals of the sensor cells covered only partially by the image of the textile material (referred to herein as edge pixels) are converted into measured values in a pro rata manner proportional to the amount of the partial covering to be taken into account in the overall measuring of the textile material.

The magnitude of the possible error and the deviation of the determined value of the textile material from its actual value is decisively reduced in a simple yet effective manner by the separate evaluation and proportional accounting for the signals of the edge pixels, i.e., the partially covered sensor cells. In particular, it is not necessary to create or even to develop special designs for sensors but rather the customary and thus economical series of known sensors can be used.

According to the principle of the invention, an absolute measurement of the yarn thickness is not performed or intended. Instead a calibration procedure is initially performed by means of establishing a standard gauge of measurement of the sensor signals against a known diameter. All further measurements of sensor signals thereafter during actual operation are made in relation to this standard gauge. Advantageously, therefore, even a blurry representation of the yarn edges does not lead to a distortion of the measured result because any such blurriness, i.e. the representation of a yarn edge as an area, even though narrow, will be present during calibration, if at all, e.g., because of the use of the optical devices, distance of the yarn from the CCD sensor, etc. It is also advantageous that, in the preferred embodiment the two opposite yarn edges result in partial coverage of only two corresponding edge pixels (i.e. sensor cells) which also contribute to the accuracy of the measurement performed under the present invention.

It is especially advantageous and simple to detect the radiation strength as a measure of the pro rata degree of coverage of the sensors. However, the measuring of the frequency of signals is also possible, for example.

It is preferable to use a light source as an economical radiation source. Further possibilities are constituted by an operation like a stroboscope or with infrared illumination with suitable sensors.

A parallel ray beam is preferably generated by the ray source since in this manner a substantially sharp delimitation is obtained between light and shadow which improves an image of the edge zones of the material to be measured. An even sharper formation of the contours is achieved with laser beams. In addition, laser beams offer advantages during optical scanning by virtue of their monochromatic light in contrast to the color mixture of a normal incandescent lamp.

In order to detect the dimensions of non-circular material to be measured an arrangement in which the material to be measured is irradiated and imaged from different directions is especially suitable.

The determination of a proportional component out of the signals of the edge pixels in combination with the high, reproducible measuring precision of line sensors such as is offered, e.g., by a CCD line sensor, is advantageous in the determination of dimensions.

It is also advantageous if an analog image of the material to be measured differing from the actual magnitude is projected onto the sensor range of the receiving device. An enlarged image covers a greater number of sensor cells or pixels and results in a higher resolution without altering the sensor cells of the receiving device. This significantly increases the measuring precision of the method without using, for example, an expensive line sensor whose sensor cells exhibit a correspondingly reduced width instead of using the economical series sensor cells. Textile material to be measured whose diameter or cross section is greater than the width of the sensor range of the line sensor used can also be detected with a reduced analog image of the material to be measured on the sensor range.

An improved proportionality factor for the measure of the covering of the edge pixels is created by the determination of differential values from the measured absolute values of the radiation strength received even taking into account disturbing influences such as stray or scattered light or foreign extraneous radiation.

The device for carrying out the method of the invention combines in an advantageous manner an electronic computational device which takes into account in the evaluation the extent of the covering of the edge pixels in a proportional manner with a device for the retransmission or further processing of the measured result and, in a further advantageous development, with an optical device for generating a parallel ray beam with which either a ray shadow is cast onto the sensor range of the receiving device or the material to be measured is imaged onto the sensor range. The measured result can also be outputted or indicated in a known manner such as, e.g., by a printer.

Further features, advantages and details of the invention will be explained and understood in more detail from exemplary embodiments described in the following specification with reference to the accompanying drawings.

DESCRIPTION OF THE PREFERRED EMBODIMENTS

Figure 1:
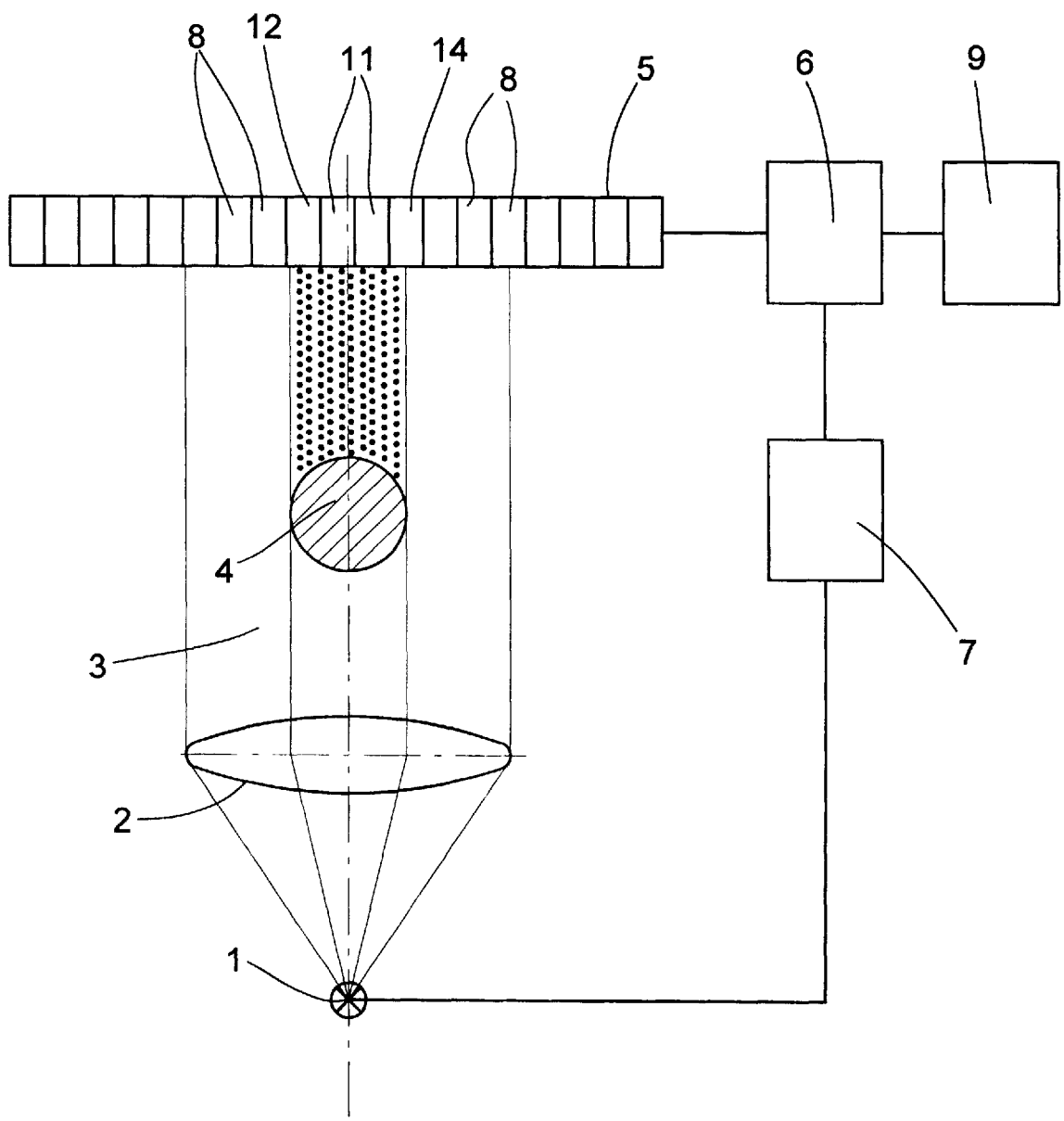
FIG. 1 is a schematic diagram depicting the principle of an arrangement for measuring yarns in accordance with the present invention.

Referring now to the accompanying drawings and initially to FIG. 1, a measuring arrangement is shown which comprises a punctual light source acting as ray source 1 whose rays are parallelized by optical device 2. Strand-like textile material to be measured 4, e.g., a yarn, passes through parallel ray beam 3, which images the textile material 4 in the form of a shadow on the sensor cells of receiving device 5. The signals produced by the individual sensor cells are separately detected and processed further in computational device 6.

Regulator 7 is connected to computational device 6 for varying the brightness of ray source 1 and thereby for producing a largely uniform brightness value for the sensor cells 8 which are not shadowed or otherwise covered. The result of the measurement is retransmitted or further processed by device 9.

Of course, as persons skilled in the art will recognize, while the embodiment herein described utilizes a light source situated at the opposite side of the yarn from the receiving device 5, it is also contemplated to be possible to situate the light source at the same side of the yarn as the receiving device 5. In such case, a background would be provided behind the yarn having a differing reflectivity to permit the sensor cells 8 of the receiving device 5 to be imaged by the ray source 1. Each such embodiment is intended to be within the scope of the present invention.

Figure 2:
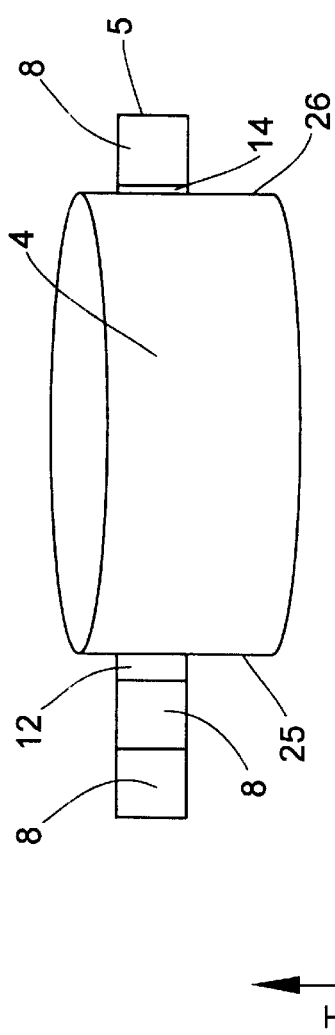
FIG. 2 is a schematic depiction of a yarn section in front of a receiving device in the performance of a measuring operation in accordance with the present invention.
Figure 3:
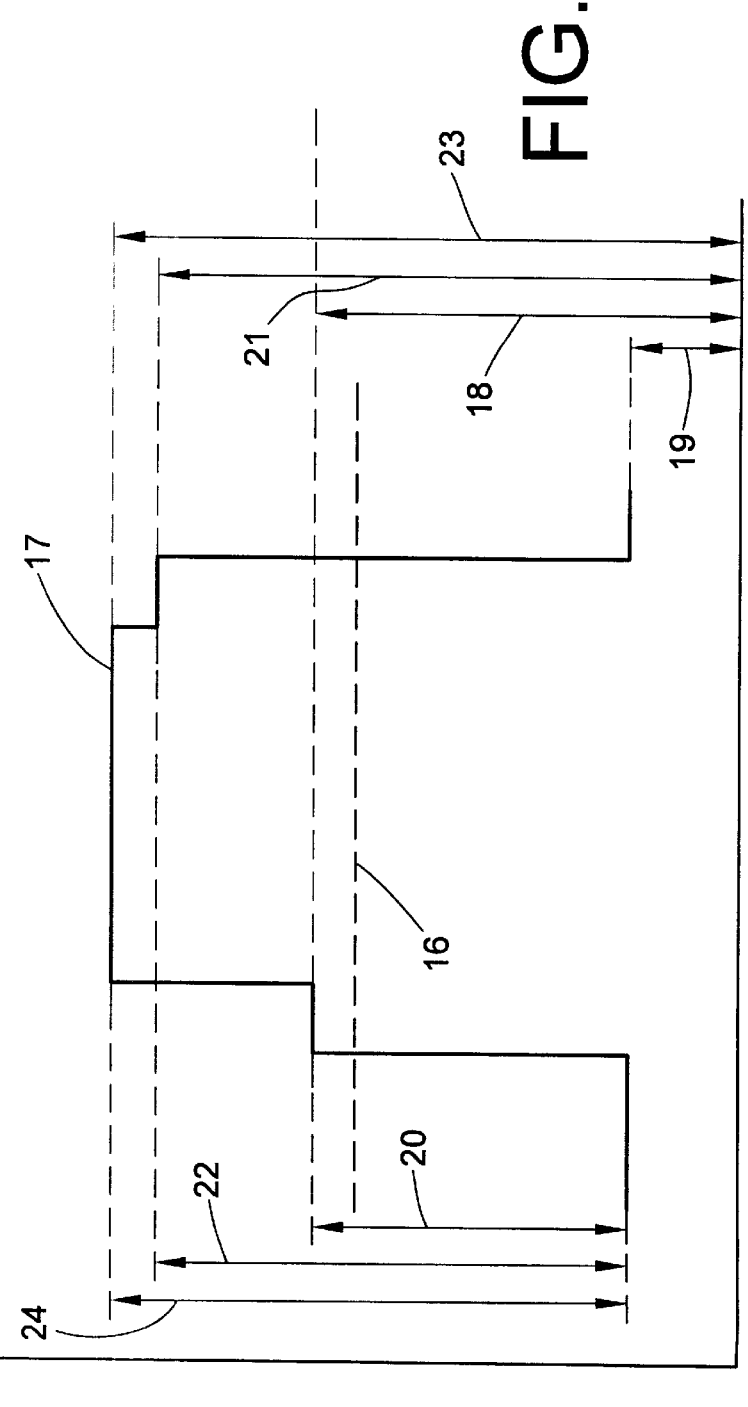
FIG. 3 is graph depicting a pulse image arising from the performance of a measuring operation in accordance with FIG. 2.

FIG. 2 shows a yarn as the strand-like textile material 4 being conducted past line sensor 10 operating in receiving device 5. The diameter of the yarn in this example is 6.5 times the width of the sensor cells, i.e., the pixels. The depicted yarn section completely covers (i.e. completely shadows) five pixels 11 (sensor cells) and partially covers two sensor cells 12, 14, such partially covered sensor cells being designated herein as edge pixels.

According to the setting of a threshold value in the previously known method described above, edge pixels 12, 14 and their signals are evaluated as completely covered or as completely irradiated sensor cells. The pulse image produced in FIG. 2 is shown as rectangular diagram 17 corresponding to the measured brightness or the covered surface of the individual sensor cells.

The level of threshold value 16 is marked by a broken line. This threshold value 16 is exceeded for both edge pixels 12, 14. Thus, in this example, the evaluation of edge pixels 12, 14 as "completely covered" results in a determination of a yarn diameter according to the known method which diameter is 7 times the width of the sensor cells and therewith produces a deviation of the measured result from the actual value of at least 8%.

The evaluation according to the method of the present invention, in contrast, takes place via a pro rata or proportional accounting for the values supplied from edge pixels 12, 14 in the measuring of the diameter of the yarn. As already noted above, an initial calibration procedure is performed against a known diameter in order to provide a base of reference by which fully covered and completely uncovered pixels can be identified and the pro rata proportional evaluation of partially covered edge pixels can be performed. Radiation values are established by which fully covered pixels and completely uncovered pixels are distinguished from partially covered pixels and from one another. Specifically, a mean radiation value is established for identifying a fully covered pixel based on values taken from all or at least a plurality of fully covered pixels and, likewise, a mean value is established for a completely uncovered pixel based on values from plural uncovered pixels.

At first, the absolute pulse value $I_{AL}$ 18 supplied from left edge pixel 12 is reduced by the absolute pulse value of background $I_{AH}$ supplied by completely uncovered pixels 8 to produce differential value $I_{RL}$ 20 according to the following formula:

$$I_{RL} = I_{AL} - I_{AH}.$$

In the same manner the absolute pulse value $I_{AR}$ 20 supplied from right edge pixel 14 is reduced by the absolute pulse value of background $I_{AH}$ 19 to produce differential value $I_{RR}$ according to the following formula:

$$I_{RR} = I_{AR} - I_{AH}.$$

The absolute pulse value $I_{AD}$ supplied from fully shadowed pixels 11 is likewise reduced by the absolute pulse value $I_{AH}$ 19 to produce differential value $I_{RD}$ 24 according to the formula $I_{RD}=I_{AD}-I_{AH}.$ The width of the sensor cells or the pixel width $B_P$ is given by the design of the sensors.

The diameter $D_G$ of the yarn calculated as measured result is composed of a component $D_L$ which results from the calculation:

$$D_L = \frac{I_{RL}}{I_{RD}} \times B_P,$$

a component $D_R$ which results from the calculation:

$$D_R = \frac{I_{RR}}{I_{RD}} \times B_P$$

as well as a component $D_D$ which results from the calculation:

$$D_D = n_D \times B_P$$

in which $n_D$ indicates the number of fully shadowed pixels 11 located between edge pixel 12 and edge pixel 14.

Accordingly, the formula for calculating the diameter of yarn $D_G$ is:

$$D_G = D_L + D_D + D_R.$$

By inserting the formulas for $D_L$, $D_D$ and $D_R$ the complete calculation may be expressed by the equation $$D_G = \frac{I_{RL}}{I_{RD}} \times B_P + n_D \times B_P + \frac{I_{RR}}{I_{RD}} \times B_P$$

and reads in a converted form:

$$D_G = \left(\frac{I_{RL}+I_{RR}}{I_{RD}} + n_D\right) \times B_P.$$

The precision of the determination of diameter is improved in such a manner by the method described that the deviation of the determined yarn diameter from the actual value is within the magnitude necessary for yarn cleaning.

Figure 4:
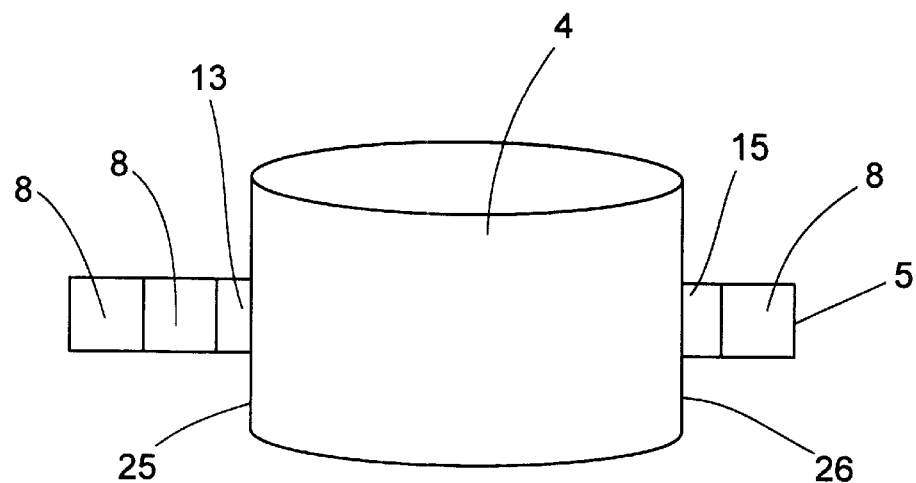
FIG. 4 is another schematic depiction of a yarn section in front of a receiving device in the performance of a measuring operation in accordance with the present invention.

FIG. 4 depicts a further exemplary embodiment. Whereas the measuring arrangement is the same as in FIG. 2, the yarn diameter is a precise multiple of the width of the sensor cells (exactly six times the width in this example).

Figure 5:
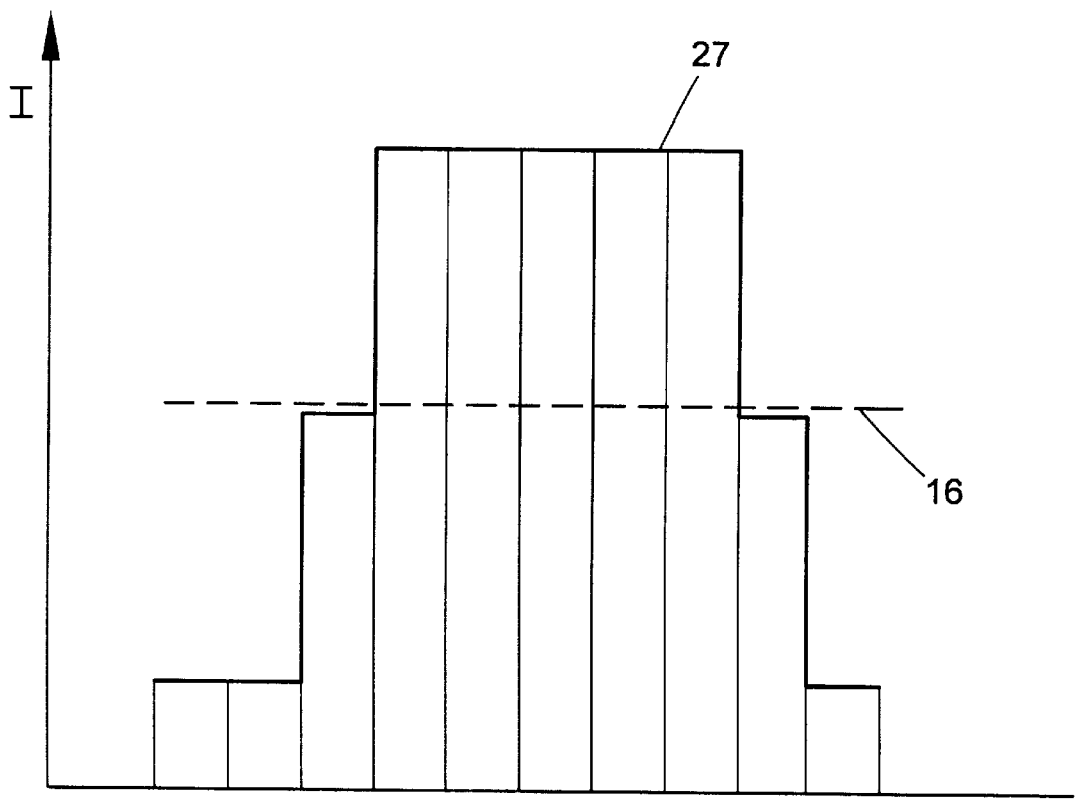
FIG. 5 is a graph depicting a pulse image arising from the performance of a measuring operation in accordance with FIG. 4.

The pulse image produced during the measuring process according to FIG. 4 is shown in FIG. 5 as column diagram 27 in order to emphasize that each sensor cell is individually evaluated.

The values supplied from edge pixels 13, 15 do not reach or exceed set threshold value 16 and therefore would not be considered as contributing in the determination of the diameter in the known threshold-value methods. If threshold value 16 were to be set lower, the value supplied from edge pixels 13, 15 would result in an evaluation of these sensor cells as "completely covered" in the known threshold-value methods. A diameter of the yarn would thereby be determined which corresponds to 5 times or 7 times the width of a sensor cell. The error which would then occur in the known threshold-value method is more than ±16% and likewise fails by far to satisfy the requirements of precision.

The precision of the determined diameter value is improved in such a manner with the method of the present invention in a simple and economical manner that the high requirements placed on the measuring precision like those occurring in yarn cleaning are met.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method for contactless measuring of a strand-like textile material of indeterminate extended length, comprising disposing the textile material within a radiation range of at least one ray source, imaging the textile material on a sensor range of a receiving device comprising sensor cells, and converting the signals produced by the individual sensor cells into measured values for the dimensions of the textile material, including converting the signals of the sensor cells receiving only partially the image of the textile material into measured values in a pro rata manner proportional to the amount of the partial imaging.

2. The method according to claim 1, wherein the converting the signals of the partially imaged sensor cells comprises determining measured values pro rata proportional to the radiation strength measured for each respective partially imaged sensor cells.

3. The method according to claim 1, and further comprising determining the dimension of the textile material from a component which is proportional to the number of sensor cells completely receiving the image of the textile material and from at least one other component which is proportional to the covering of at least one partially imaged sensor cell.

4. The method according to claim 1, and further comprising detecting and evaluating no more than one partially imaged sensor cell per side of the textile material to be measured.

5. The method according to claim 1, and further comprising generating an at least approximately parallel ray beam as the ray source.

6. The method according to claim 1, and further comprising generating a light source as the ray source.

7. The method according to claim 6, and further comprising generating a laser beam as the ray source.

8. The method according to claim 1, and further comprising providing a CCD line sensor as the receiving device.

9. The method according to claim 1, and further comprising projecting an analog image of the textile material deviating from actual size onto the sensor range of the receiving device.

10. The method according to claim 1, and further comprising determining the value for the received radiation strength and the pulse sequence of a partially imaged sensor cell by reducing a radiation value of the partially imaged sensor cell by a radiation value of a sensor cell not imaged by the textile material to produce a differential value and dividing the differential value thereby obtained by another differential value produced by subtracting the radiation value of the unimaged sensor cell from the radiation value of a sensor cell completely imaged by the textile material.

11. The method according to claim 1, and further comprising automatically regulating the radiation strength of the ray source in order to compensate for aging; fluctuations in voltage; contamination phenomena in the ray source, the optical arrangement used to generate the ray source or in the sensor cells; and other disturbing factors.

12. A device for contactless measuring of a strand-like textile material of indeterminate extended length, comprising a ray source having a radiation range, a device for moving the textile material to be measured in longitudinal direction transversely through the radiation range of the ray source, a receiving device comprising a sensor range defined by individual sensor cells for generating electric signals, the receiving device being arranged for generating an image of the textile material by the radiation of the ray source on the sensor range of the receiving device, an electronic computational device for measuring the signals of the sensor cells receiving only partially the image of the textile material in a pro rata manner proportional to the amount of the partial imaging and for retransmitting or further processing the measured value of the signals of the partially imaged sensor cells in a pro rata manner proportional to the amount of the partial imaging.

13. The device according to claim 12, and further comprising an optical device for generating a parallel ray beam.

14. The device according to claim 12, and further comprising an optical device for generating an image of the textile material on the sensor range of the receiving device.

* * * * *